United States Patent [19]

Dolby et al.

US005675038A

[11] Patent Number: 5,675,038
[45] Date of Patent: Oct. 7, 1997

[54] LITHIUM AND AMINE DISSOLVING METAL REDUCTION

[75] Inventors: Lloyd J. Dolby; Nestor A. Fedoruk; Shervin Esfandiari; Natalie C. Chamberlain, all of Eugene, Oreg.; Michael E. Garst, Newport Beach, Calif.

[73] Assignee: Allergan, Waco, Tex.

[21] Appl. No.: 685,902

[22] Filed: Jul. 18, 1996

[51] Int. Cl.$^6$ .................................................. C07C 291/00
[52] U.S. Cl. ........................... 564/253; 568/303; 585/267
[58] Field of Search ........................... 585/267; 564/253; 568/303

[56] References Cited

U.S. PATENT DOCUMENTS

| | | | |
|---|---|---|---|
| 3,470,197 | 9/1969 | VanDyke, Jr. | 260/309 |
| 5,055,467 | 10/1991 | Albaugh | 514/235.8 |
| 5,198,545 | 3/1993 | Albaugh | 544/133 |
| 5,264,449 | 11/1993 | Albaugh | 514/397 |
| 5,453,434 | 9/1995 | Albaugh et al. | 514/397 |

OTHER PUBLICATIONS

DeGraw, J.L., "Prostaglandins, An Improved Synthesis of Pilocarpine," Tetrahedron, vol. 28, 1972, pp. 967–972.
Koda et al, "Synthesis of Analogs related to Pilocarpine", Journal of Pharmaceutical Sciences, Dec. 1973, vol. 62, No. 12, pp. 2021–2023.
Sauerberg et al, "Cyclic Carbamate Analogues of Pilocarpine", J. Med. Chem. 1989, 32, pp. 1322–1236.
Kondo et al, "Synthesis of y-Lactones By The Condensation of 2-Alkene-1, 4-Diols With Orthocarboxylic Esters", Chemistry Letters, pp. 741–742, 1974.
Noordam et al, "Stereoselective synthesis (+)-pilocarpine, an imidazole alkaloid used in ophthalmology", Recl. Trav. Chim. Pays–Bas 98, pp. 425–470.
Dey, A.N., "The Jaborandi Alkaloids. Part I. The Synthesis of Homo–and isoHomo–pilopic Acids of r–Pilocarpine and r–isoPilocarpidine by New Methods and the Resolution of r–Pilocarpine", S. Chem. soc., (1937), pp. 1057–1065.
Birch et al, "Reduction by Metal–Ammonia Solutions and Related Reagents", Advanced Organic Chemistry, No. 8, pp. 1–65 (1972).
Benkeser et al, "Reduction of Organic Compounds by Lithium in Low Molecular Weight Amines. VII. The Preparation of Dihydroaromatics. A Comparison of the Lithium–Amine and Birch Reduction Systems", Journal of Organic Chemistry, 28, pp. 1094–1096, 1972.
Kaiser, E.M., "A Comparison of Methods Using Lithium/Amine and Birch Reduction Systems", Synthesis, 1972, pp. 391–415.

*Primary Examiner*—Mukund J. Shah
*Assistant Examiner*—Bruck Kifle
*Attorney, Agent, or Firm*—James M. Hoch; Robert J. Baran; Martin A. Voet

[57] ABSTRACT

The invention is directed to a process for reducing or reductively cleaving an organic compound susceptible to dissolving metal reduction comprising exposing the organic compound to a solution of lithium in a polyamine including at least two amino groups, selected from the group consisting of primary and secondary amino groups and mixtures thereof, e.g. ethylenediamine and R—$NH_2$, optionally containing a lower alkyl alcohol, wherein R is chosen from the group consisting of ethyl, propyl, and butyl, including all straight and branched chain isomers thereof, for a time sufficient to effect reduction.

35 Claims, No Drawings

LITHIUM AND AMINE DISSOLVING METAL REDUCTION

CROSS REFERENCE TO RELATED APPLICATIONS

Commonly assigned U.S. patent application Ser. No. 08/685,897, entitled "Process for Making Pilolactam and Derivatives Thereof" which has been filed on the same day as the present application in the names Lloyd J. Dolby, Nestor A. Fedoruk, Shervin Esfandiari, and Michael E. Garst is directed to a process of making an intermediate for the synthesis of isopilolactam, pilolactam and derivatives thereof. The contents of this copending application are incorporated herein by reference in its entirety.

BACKGROUND OF THE INVENTION

FIELD OF THE INVENTION

The invention described herein relates generally to the field of reductive hydrogenation of organic compounds. In particular, the invention relates to the treatment of organic compounds by lithium in a mixture of a lower molecular weight amine and a polyamine including at least two amino groups, selected from the group consisting of primary and secondary amino groups and mixtures thereof, e.g. ethylenediamine, to effect reduction.

BACKGROUND OF THE ART

Reductions using alkali metals in ammonia or lower alkyl amines are synthetically useful reactions for the reduction of organic compounds. The metals commonly employed include the alkali metals—lithium, sodium and potassium—as well as calcium and magnesium and occasionally zinc and iron. The alkali metals and calcium dissolve into solutions in liquid ammonia (b.p. −33° C.), in low molecular weight amines such as methylamine and ethylamine, or in certain ethers such as 1,2-dimethoxyethane. Reactions with metal solutions in liquid ammonia often use a cosolvent such as ether, tetrahydrofuran, or 1,2-dimethoxyethane to increase the solubility of the organic substrate in the reaction mixture. This sometimes has the disadvantage of resulting in a two phase reaction mixture.

The Birch reduction is perhaps the best known form of these metal reductions and utilizes sodium metal, liquid ammonia, and an alkyl alcohol such as n-butanol or t-butanol. The Benkeser reduction is another form of the reduction which utilizes lithium metal and a lower alkyl amine along with one of the already mentioned alcohols. These reductions as a class are called dissolving metal reductions; this term being descriptive since the metals dissolve into solution which is generally blue in color as a result of ionization of the metal atoms.

A proton source (frequently ethanol, isopropanol, t-butanol, or water) may be necessary and present in the reaction medium, and is added concurrently with the compound to be reduced, or is added during the isolation.

An early hypothesis that dissolving metal reductions were effected by reaction of the 'nascent' hydrogen liberated from reduction of the hydroxylic solvent by the metal with the molecule being reduced has since been dismissed as untenable. In fact, the formation of hydrogen gas during these reactions is normally an undesirable side reaction which makes the use of excess metal necessary. Presently it is believed that "solvated" electrons in the solution add to the substrate to form a radical anion which can add a proton from the solvent to form a radical which can in turn add another electron to form a further reduced anion and so forth until the reaction has reached completion. Alternatively, without an acidic proton source (i.e. a source of protons more acidic than ammonia or alkylamine) the reaction may proceed via a different route to form a less reduced or isomerically different product.

The use of lithium in a mixed solution of lower alkyl amine and a polyamine, such as ethylenediamine, is a very potent reducing system which may be attributable to the superior electron solvating ability of the ethylenediamine/alkyl amine solvent mixture.

A. J. Birch and G. Subba Rao reviewed many types of dissolving metal reductions in a monograph entitled "Reduction by Metal-Ammonia Solutions and Related Reagents" in *Advanced Organic Chemistry*, No. 8, pp. 1–65 (1972).

R. A. Benkeser, et al., [*Journal of Organic Chemistry*, 28, pp. 1094–96 (1962)] described the use of low molecular weight amines in lithium metal reductions and compared the yields and regioisomers to reductions of the same group of compounds using Birch reduction conditions.

Edwin M. Kaiser wrote a review entitled "A Comparison of Methods Using Lithium/Amine and Birch Reduction Systems" [*Synthesis*, 1972 pp. 391–415] which also compares reports of yields and conditions for these two reaction types.

SUMMARY OF THE INVENTION

The invention is directed to a process for reducing or reductively cleaving an organic compound susceptible to dissolving metal reduction comprising exposing the organic compound to lithium in a mixed solution of a polyamine including at least two amino groups, selected from the group consisting of primary and secondary amino groups and mixtures thereof, wherein said polyamine comprises from 2 to 4, e.g. 2, nitrogen atoms and from 2 to about 30, e.g. from 2 to about 20 carbon atoms, and may be selected from the group consisting of alkyl and cycloalkyl amines such as ethylenediamine, N,N'-dimethylethylenediamine, piperazine, diaminopropane, diaminobutane, dimethyl diaminobutane, tris-(aminoethyl) amine, etc., e.g ethylenediamine, and R—$NH_2$ wherein R is selected from the group consisting of lower alkyl radicals, having from 2 to 6 carbon atoms, preferably ethyl, propyl, and butyl, including all straight and branched chain isomers thereof, optionally containing a lower alkyl alcohol, for a time sufficient to effect reduction.

The present process for reducing susceptible organic chemical compounds uses lithium metal as an electron source, the above lower alkyl amines as solvent and the above polyamine, e.g. ethylenediamine (1,2-diaminoethane), as the cosolvent. Lithium is dissolved in the alkyl amine along with at least one equivalent of said polyamine, e.g. ethylenediamine, per gram-atom of lithium. Optionally, a lower alkyl alcohol can be added to the solution to improve yields of desired products. A discussion of these protonation mechanisms and reaction kinetics can be found in the review on dissolving metal reductions by Birch, et al. (vide supra).

Examples of compounds susceptible of being reduced or reductively cleaved by this system (products follow in parentheses) are: anisoles (methoxycyclohexadienes), naphthalenes (isotetralins), α,β-unsaturated ketones (ketones), ketoximes (amines), aldoximes (amines), thioanisoles (thiophenols), reduction of tertiary amides, cleavage of sulfonate esters (to the alcohols) and reductions of p-toluenesulfonamides (to amines, or in the case of tertiary sulfonamides to the thiophenol).

DETAILED DESCRIPTION OF THE INVENTION

Preliminary experiments with lithium in lower alkyl amines alone, such as in n-propylamine or isopropylamine made clear that reduction is very slow and subsequently the yields are not as high. Essentially the reaction does not proceed without the addition of a polyamine, such as ethylenediamine, to the reaction mixture. The addition results in reaction times that are faster than comparable reductions done under Birch conditions or lithium in amine (Benkeser) conditions. At least one mole of polyamine, e.g. ethylenediamine, per gram atom of lithium is used in reactions utilizing the processes of the present invention, optionally more than one equivalent may be added. The present invention may be carried out without any hydroxylic Solvent, but in some reactions, an added hydroxylic solvent, such as t-butanol, may be beneficial to the yield of a desired product or isomer of a product. Addition of an alcohol provides a source of protons more acidic than the amine groups present in the reaction solution. This can assist in protonation of intermediates or products in the reaction and so speed the reaction, reduce formation of unwanted by-products or isomers, or allow the reduction to proceed beyond that which would occur without protonation of an intermediate. One skilled in the art can determine when such addition is beneficial, either through the analysis of the predicted reaction mechanism or through experimentation.

Temperatures at which the reaction can be run vary from −20° C. to 65° C. Preferred temperatures for the practice of the present invention are from 0° C. to 55° C., with the most preferred temperature being at or about room (ambient) temperature. The reaction is run at ambient (atmospheric) pressure, and so, in any case, the reaction temperature cannot be above the boiling point of the reaction solution chosen.

Preferred alkyl amines for use in the present invention are n-propylamine, isopropylamine and t-butylamine. Most preferred of these amines for use in the present process is n-propylamine, however, t-butylamine is preferred when there is a need for a non-nucleophilic amine such as in reductions of N-benzyl-amides. The more lipophilic nature of these alkyl amines causes better solubility of the organic substrate.

The order of addition of the reactants to the alkyl amine-polyamine, e.g ethylenediamine, solvent can vary. Lithium can be added first to the mixture, or in portions after addition of the organic substrate. If the reaction is exothermic, solvent can easily be returned to the reaction mixture by equipping the reaction flask with a water-cooled reflux condenser.

Reaction times vary with different conditions and substrates being reduced, but are of sufficient length to allow the starting materials to be reduced to the desired products, but not of such a length of time to allow unwanted double bond isomerizations or side reactions to occur. Monitoring of reaction progress is routinely conducted in the practice of synthetic chemistry and varies with the We of reaction. Examples of methods used in monitoring are thin layer chromatography, proton NMR, fluorescence spectrophotometry and measurement of solution pH. One skilled in the art knows which method to select depending on the starting materials, products and conditions utilized in running the reaction. Generally, after all of the lithium metal has dissolved into the solvent, the reaction is considered to have finished. Time spans of between 5 minutes and 24 hours are typically required.

Once the reaction is complete, the solvent phase is customarily removed under reduced pressure, typically on a rotary evaporator, which allows recovery of the solvents from the reaction mixture. After evaporation, a semisolid or viscous oil remains. This residue is treated with water, which in some reactions can be quite exothermic, to dissolve or dilute the residue. An organic solvent that is immiscible in water yet has the necessary solubilization characteristics to dissolve the product of the reaction is then added to the aqueous mixture. One skilled in the art of synthetic chemistry is knowledgeable in the selection of suitable solvents for the dissolution and extraction of a given compound or class of compounds.

The aqueous phase is extracted one or more times with the selected solvent and the organic phases are combined, dried and the solvent is removed under reduced pressure or by distillation at low pressure. The resulting products can either be oils or solids. Oils, if of sufficient stability, can be distilled under vacuum. Otherwise column chromatography may be employed in obtaining the product in purified form. Solids can be recrystallized from a suitable solvent or combination of solvents to effect purification.

One advantage of this reduction system is the faster reaction times that are obtained with the addition of a polyamine, such as ethylenediamine, to the lower molecular weight amine solvent.

Another advantage is obviation of the need to wait for liquid ammonia or methylamine to evaporate from the reaction mixture after the reduction is completed, as is the case with other reduction conditions. The use of higher boiling amines allows for their recovery and recycling from the reaction mixture.

A still further advantage is that using an aliphatic amine permits solubilization of the organic substrate without ether or tetrahydrofuran which avoids the use of highly flammable ether co-solvents, and also the possibility of two phase reaction mixtures.

Another further advantage is that the reaction may be run at or around room temperature, instead of having the necessity for low temperature apparatus, such as Dewar condensers, and fume hoods to remove ammonia or methylamine as it evaporates. Ammonia boils at −33° C. and methylamine at −6.3° C. while ethylamine, the lowest boiling of the amines useful in the present invention boils at 16.6° and the highest boiling, n-butylamine, at 78°. Room temperature (68° F.) converts to 20° C. n-Propylamine has a bp of 48°–49° C. and isopropylamine has a bp of 33°–44° C.

The reaction can be conveniently carried out on a variety of saturated compounds (i.e. compounds without carbon—carbon double bonds) to reduce susceptible functional groups or to cleave them, and on unsaturated compounds to reduce some or all of the double bonds present, or on molecules which contain both susceptible functional groups and carbon-carbon unsaturated bonds, such as α, β-unsaturated ketones. The following examples are given for the purposes of illustration of the invention and should not be construed as limiting the scope of the present invention.

EXPERIMENTAL

All reductions were carried out under nitrogen. Proton magnetic resonance spectra were measured at 60 MHz using a Varian T-60 NMR spectrometer. Materials were analyzed by glpc on a Hewlett Packard model 5890 gas chromatography instrument equipped with a thermal conductivity detector using helium as carrier gas. Column: HP-5, 10M× 530 microns (unless otherwise noted).

EXAMPLE 1 trans-N-Benzylpilolactam. A solution of pilocarpine hydrochloride (98 g, 0.40 mol) and 300 g (2.8 mol) of freshly distilled benzylamine was heated under reflux in a nitrogen atmosphere for 40 hr. After 22 hr, the reaction mixture contained about 12% of pilocarpine. The cooled reaction mixture was treated with 100 mL of 3N sodium hydroxide and the layers were separated. The aqueous layer was washed with two 100 mL portions of dichloromethane. The combined organic material was washed twice with water, and the dichloromethane was evaporated. The benzylamine was distilled finally at 75° (15 mm). The gas chromatogram of the residue, 140 g, showed 2% pilocarpine, 74% trans-N-benzylpilolactam, and 10% of material eluting near the major product which might be the cis-isomer. The remaining material was a number of minor impurities. The crude material was used for the next step.

EXAMPLE 2 trans-Pilolactam. Debenzylation with lithium in n-propylamine. A solution of N-benzylpilolactam (29.7 g, 0.1 mol) in 400 mL of n-propylamine and 40 mL of ethylenediamine in a three-neck flask fitted with a mechanical stirrer under nitrogen was cooled to 0° an ice bath. Lithium (7.0 g, 1.0 gram-atom) in small pieces was added quickly. After 20 min the internal temperature rose to 20° and remained there for an hour. When the temperature began to drop, the ice bath was removed. After an additional 4 hr all of the lithium was gone. The reaction develops a deep maroon color. The volatile amines were evaporated under reduced pressure and 300 mL of cold water was cautiously added to the residue (very exothermic). The aqueous solution was extracted three times with 100 mL portions of ether which removed the majority of the impurities and only a trace of the product. Three extractions with 100 mL portions of chloroform afforded 19 g of crude product after evaporation of the solvent. The gas chromatogram showed 93% of trans-pilolactam. The crude lactam was dissolved in 50 mL of acetone and filtered to remove 0.2 g of insoluble material. Another 50 mL of acetone was added and the solution was cooled in an ice bath. A solution of p-toluenesulfonic acid (20 g) in 50 mL of acetone was added dropwise over 20 min to the magnetically stirred solution. Stirring was continued for another 20 min and then the mixture was filtered to give 17.6 g (50% for two steps) of trans-pilolactam p-toluenesulfonate salt. If the p-toluenesulfonic acid is added rapidly to the crude base, the salt separates first as a viscous oil and a less pure product is obtained. The free base may be obtained from the salt in essentially quantitative yield by treatment with aqueous sodium hydroxide and extraction with chloroform.

EXAMPLE 3

Amides of n-decanoic acid. The N-benzyl-N-methyl, N-methyl, N-propyl, and N-(2-aminoethyl)amides of n-decanoic acid were all prepared by treating n-decanoyl chloride with the appropriate amine in pyridine. The amides could be purified by crystallization or distillation under reduced pressure.

EXAMPLE 4

Reduction of N-benzyl-N-methyldecanoic acid amide.

A. n-Propylamine and ethylendiamine solution. A solution of N-benzyl-N-methyldecanoic acid amide (2.76 g, 10 mmol) in n-propylamine (30 mL) and ethylenediamine (3.6 g, 60 mmol) was cooled to −18°. Lithium (0.42 g, 0.06 gram-atom) was added in small pieces. The reaction mixture warmed to −8° and then cooled to −10°. After 1 hr, the reaction mixture turned blue and glpc analysis of an aliquot indicated complete reaction. The reaction mixture was poured onto a mixture of 50 g of ice and 50 mL of water and extracted with ether (2×50 mL). The combined ether extracts were washed with water (1×50 mL) and brine (1×50 mL) and the ether was evaporated under reduced pressure to give an oil (1.8 g). The crude product was crystallized from hexane (25 mL) with cooling to 0° to give 1.3 g (70%) of N-methyldecanamide. Glpc analysis indicated N-methyldecanoic acid amide (94%) contaminated with N-propyldecanoic acid amide (1%), and N-(2-aminoethyl) decanoic acid amide (5%).

B. t-Butylamine and ethylenediamine solution. A solution of N-benzyl-N-methyldecanoic acid amide (0.55 g, 2 mmol) in t-butylamine (8 mL) and ethylenediamine (0.72 g, 12 mmol) was cooled to −18° and lithium (0.084 g, 12 mmol), in small pieces, was added rapidly. After 2 hr the reaction mixture was allowed to warm to room temperature. After 5 hr, an aliquot of the reaction mixture showed 75% of N-methyldecanoic acid amide and 17% of N-(2-aminoethyl) decanoic acid amide.

C. t-Butylamine and N,N'-dimethylethylenediamine solution. A solution of N-benzyl-N-methyldecanoic acid amide (2.75 g, 10 mmol) in t-butylamine (30 mL) and N,N'-ethylenediamine (5.3 g, 60 mmol) was cooled in an ice bath. Lithium (0.42 g, 0.06 gram-atoms) in small pieces was added at once. After 11 hr, the reaction mixture was poured into a mixture of 1M hydrochloric acid (100 mL) and ice (50 g). The crystalline product was collected by filtration and washed with water (50 mL). The crude N-methyldecanoic acid amide (1.3 g, 70%) was 91% pure by glpc. The material was stirred with 0.5M hydrochloric acid (20 mL), filtered and dried to give 1.14 g (61%) of product which was 96.4% pure by glpc. The crude amide was recrystallized from 7 mL of hexane, cooled to freezer temperature, to give 1.07 g (58%) of N-methyldecanoic acid amide which was more than 99% pure by glpc.

D. n-Propylamine solution with t-butanol. A solution of N-benzyl-N-methyldecanoic acid amide (10 g, 0.036 mol) in n-propylamine (100 mL), ethylenediamine (13 g, 0.216 mol) and t-butanol (16 g, 0.216 mol) was cooled to −18° and lithium (1.77 g, 0.252 mol), in small pieces, was added rapidly. After 15 min, the temperature raised to 12° and then lowered. After another 45 min, the reaction turned blue and after another 30 min a yellow solution was obtained. The reaction mixture was poured over 75 g of crushed ice and water (75 mL). The mixture was extracted with ether (2×75 mL) and the combined ether extracts were washed with brine (2×50 mL). The ether was evaporated and the residue was dissolved in THF (50 mL) and 3N hydrochloric acid (15 mL). The solution was heated under reflux for 2 hr and then cooled and diluted with brine (50 mL). The mixture was extracted with ether (2×75 mL) and the combined ether extracts were washed with brine (1×50 mL) and filtered through 1PS filter paper. The ether was evaporated and the residue was distilled to give 2.0 g (36%) of n-decanal having a bp 100°–105° (15 mm).

EXAMPLE 5

Reduction of anisole. Lithium, in small pieces, (8.75 g, 1.25 gram-atoms) was added to a solution of anisole (54 g, 0.5 mol) in n-propylamine (400 mL), ethylenediamine (105 g (1.75 mol) and t-butanol (111 g, 1.5 mol) cooled to −18°. The temperature increased to 12° and then decreased to −5°. After 2 hr all of the lithium had reacted and the reaction mixture was diluted with 800 mL of water added slowly. The mixture was extracted with ether (3×250 mL). The ether extracts were washed with water (3×200 mL) and brine (1×100 mL) and evaporated. The residue was distilled to give 27.5 g (50% of 1-methoxy-1,4-cyclohexadiene containing 10% of 1-methoxy-1,3-cyclohexadiene by glpc and nmr.

EXAMPLE 6

Reduction of naphthalene. Lithium (3.5 g, 0.5 gram-atom), in small pieces, was added in one portion to a solution, cooled to −16°, of naphthalene (12.8 g, 0.10 mol) in n-propylamine (100 mL), ethylenediamine (30 g, 0.5 mol) and t-butanol (44.4 g, 0.6 mol). The solution warmed to 45° and cooled to 0° in 15 min. After 15 min, the reaction mixture was poured over 150 g of ice and 100 mL of water and then extracted with ether (3×150 mL). The ether was washed with water (2×100 mL) and brine (1×100 mL). The ether was evaporated under reduced pressure to give 12.2 g of a colorless solid which was triturated with methanol, filtered and dried to give crude 1,4,5,8-tetrahydronaphthalene which was crystallized from methanol (25 mL) to give 8.6 g (65%) of 1,4,5,8-tetrahydronaphthalene which was 93% pure by glpc.

EXAMPLE 7

Reduction of 3-methyl-2-cyclohexen-1-one. Lithium (0.154 g, 0.022 gram-atom) was added to a solution of 3-methyl-2-cyclohexen-1-one (1.1 g, 0.01 mol) in n-propylamine (10 mL) and ethylenediamine (1.32 g, 0.022 mol) at 0°. After 1.5 hr, the reaction was diluted with water (25 mL) and extracted with ether (2×25 mL). The ether was washed with brine and evaporated under reduced pressure to give a quantitative yield of 3-methylcyclohexanone which showed an nmr spectrum identical with that of authentic material.

EXAMPLE 8

Reduction of 4-methylcyclohexanone oxime. In a three-neck flask fitted with a condenser, mechanical stirrer and a thermometer was placed a solution of 4-methylcyclohexanone oxime (12.7 g, 0.1 mol) in 100 mL of n-propylamine and ethylenediamine (30 g, 0.50 mol). Lithium (3.5 g, 0.5 gram-atom), in small pieces, was added all at once. After about 25 min, the temperature rose to 55° and the mixture refluxed briskly. After 1 hr, the reaction was blue-green and all of the lithium had reacted. The reaction mixture was mixed with 200 g of ice and extracted with ether (3×100 mL). The ether solution was washed with 15% sodium hydroxide (100 mL) and brine (2×100 mL) and then dried over magnesium sulfate. The ether was evaporated and the residue was distilled to give 7.9 g (70%) of 4-methylcyclohexylamine, bp 148°–150° (atm), which was 93.5% trans and 6.5% cis by glpc on a J&W column, CDXB, 30M×0.25 mm. at 100°.

EXAMPLE 9

Reduction of 4-methylcyclohexanone O-methyloxime. A solution of 4-methylcyclohexanone. O-methyloxime (21.15 g, 0.15 mol) in n-propylamine (150 mL), ethylenediamine (72 g, 1.2 mol) and t-butanol (89 g, 1.2 mol) was treated with lithium (8.4 g, 1.2 gram-atoms) added in two portions. Addition of half of the lithium caused a temperature rise to 62° and vigorous reflux. After the reaction subsided and the reaction cooled to 50°, the remaining lithium was added which cause another exotherm and vigorous reflux. After the blue color dissipated, the reaction mixture was poured onto 100 g of ice. The mixture was extracted with hexane; the combined hexane extracts were washed with brine and filtered through 1PS filter paper. After distillation of the hexane at atmospheric pressure, 4-methylcyclohexylamine (12.6 g, 72%), bp 148–150° (atm) was obtained after distillation through a short Vigreux column.

EXAMPLE 10

Reduction of n-heptanal oxime. In a 1 L 3-neck round bottomed flask fitted with a condenser and a thermometer were placed n-heptanal oxime (28.5 g, 0.22 mol), n-propylamine (280 mL), t-butanol (32.6 g, 0.44 mol), and ethylenediamine (66 g, 1.1 mol). The reaction was run under nitrogen. Lithium (7.7 g, 1.1 gram-atoms) was added in two portions. Addition of one-half of the lithium raised the temperature to 53° and after the reaction mixture cooled to 40° the remaining lithium was added. The reaction refluxed and turned blue. After the color dissipated, the reaction mixture was poured onto ice and the resulting solution was filtered. The filtrate was treated with solid sodium hydroxide until layers formed. The organic layer was treated with solid sodium hydroxide and decanted. The organic layer was partitioned between 200 mL of hexane and 200 mL of saturated brine to remove the ethylenediamine. The brine was extracted with hexane (200 mL) and the hexane solutions were combined. The hexane was distilled through a short Vigreux column leaving 19 g of crude n-heptylamine. The original aqueous layer was extracted with ether (2×100 mL) and the ether was distilled through a short Vigreux column. The residue from the ether was partitioned between 50 mL of hexane and 50 mL of brine. The hexane was distilled through a short Vigreux column and the residue was combined with the material from the organic layer. Distillation through a short Vigreux column yielded 13.8 g (55%) of pure n-heptylamine, bp 152–158° (atm).

EXAMPLE 11

Reduction of n-nonanal O-methyloxime. Lithium (1.6 g, 0.228 mol) was added in one portion to a solution of n-nonanal O-methyloxime (5.13 g, 0.030 mol) in n-propylamine (50 mL), ethylenediamine (9 g, 0.15 mol) and t-butanol (11 g, 0.15 mol). After 3 hr, an aliquot was analyzed by glpc and no oxime was present. The reaction mixture was poured into ice-water (150 mL) and the mixture was extracted with ether (3×100 mL). The combined ether extracts were washed with brine (4×100 mL), dried over magnesium sulfate and concentrated under reduced pressure. Distillation of the residue afforded n-nonylamine (3.0 g, 70%), bp 98–100° (20 mm). The nmr spectrum was identical with that of an authentic sample.

EXAMPLE 12

Reduction of undecanenitrile in n-propylamine and ethylene-diamine. Lithium, (0.21 g, 30 mmol) in small pieces, was added to a stirred solution of undecanenitrile (0.84 g, 5 mmol) in n-propylamine and ethylenediamine (1.0 mL). The temperature began to rise after 20 min and reached 32° after 30 min and the reaction mixture turned blue. An aliquot of the reaction mixture showed no nitrile by glpc. The reaction mixture was poured over crushed ice and extracted with ethyl acetate (2×50 mL). After distillation of the ethyl acetate the residue deposited crystals. The crystals were collected and dried to give 2-(n-decyl)imidazoline (0.23 g, 22%)

EXAMPLE 13

Reduction of undecanenitrile in n-propylamine, ethylenediamine, and t-butanol. Lithium, (0.28 g, 40 mmol) in small pieces, was added to undecanenitrile (0.775 g, 4.63 mmol) in n-propylamine (10 mL), ethylenediamine (1.5 g, 25 mmol) and t-butanol (2.22 g, 30 mmol). After 20 min, the temperature increased to 55° and decreased slowly. After another 2 hr, the reaction mixture was poured onto a slurry of water (25 mL) and ice (25 g). The reaction mixture was extracted twice with ether (25 mL and 50 mL). The ether extract was analyzed by glpc using ethyl benzoate as internal standard. Glpc analysis showed n-decane in 17% yield and undecylamine in 83% yield. A similiar reaction using methanol in place of t-butanol in the same mole ratio gave the same percentages of n-decane and undecaneamine.

EXAMPLE 14

Reaction of n-undecanenitrile with ethylenediamine. A solution of ethylenediamine (9.0 g, 0.15 mol) in tetrahydrofuran (25 mL) in a three-neck flask fitted with a mechanical stirrer, and a thermometer was cooled to −20°. A solution of n-butyllithium (14.4 mL of 2.5M in hexane, 0.036 mol) was added over 5 min and after an additional 10 min, n-undecanenitrile (5.0 g, 0.03 mmol) in tetrahydrofuran (10 mL) added over 15 min. The cooling bath was removed and the reaction mixture was stirred at room temperature for another 30 min. An aliquot of the reaction mixture showed no n-undecanenitrile by glpc. Water (25 mL) was added to the reaction mixture and it was extracted with ethyl acetate (2×50 mL). The ethyl acetate extracts were washed with brine (2×25 mL), filtered through IPS filter paper and concentrated under reduced pressure to give a solid (6.5 g). The material was triturated with hexane (25 mL) and filtered to give 2-(n-decyl)-2-imidazoline (5 g, 79% after drying). Glpc analysis showed a purity of 100%.

EXAMPLE 15

Reaction of benzonitrile with ethylenediamine. A solution of ethylenediamine (15 g, 0.25 mol) in tetrahydrofuran (40 mL) in a three-neck flask fitted With a mechanical stirrer, and a thermometer was cooled to −20°. A solution of n-butyllithium (24 mL of 2.5M in hexane, 0.06 mol) added over 10 min and after 30 min, benzonitrile (5.15 g, 0.05 mol) added over 15 min. Cooling bath was removed and the reaction mixture stirred at room temperature for another hour. An aliquot of the reaction mixture showed no benzonitrile by glpc. Water (50 mL) was added to the reaction mixture which contained gummy material. The mixture was extracted with ethyl acetate (2×60 mL). The ethyl acetate extracts were washed with brine (2×25 mL), filtered through IPS filter paper and concentrated under reduced pressure to give a solid (6.1 g). The crude product crystallized from acetone (10 mL) to give 5 g (68%) of 2-phenyl-2-imidazoline, which was 100% pure by glpc.

EXAMPLE 16

Reduction of thioanisole. Thioanisole (1.24 g, 0.01 mol) in n-propylamine (10 mL) and ethylenediamine (1.8 g, 0.03 mol) at 0° was treated with lithium (0.21 g, 0.03 gram-atom). The reaction mixture turned dark blue. After 1 hr the ice bath was removed, and the reaction was continued for 3 hr at room temperature. The reaction mixture was then poured onto concentrated hydrochloric acid (25 mL) and ice (25 g). The mixture was extracted with ether (2×75 mL). The ether solution was dried over sodium sulfate and evaporated to give 0.9 g (82%) of thiophenol which was 90% pure by glpc (6% thioanisole).

EXAMPLE 17

Reduction of morpholine p-toluenesulfonamide. Lithium (3.9 g, 0.56 gram-atom) was added in two portions to a solution of morpholine p-toluenesulfonamide (15 g, 0.062 mol) in n-propylamine (250 mL), ethylenediamine (37 g, 0.62 mol) and t-butanol (9.2 g, 0.12 mol) at room temperature. One half of the lithium was added and after an hour most of it had dissolved and the second portion was added. The reaction was continued to another 3.5 hr and then cooled in an ice bath and treated with methanol (30 mL). Water (120 mL) was added and the reaction mixture was evaporated under reduced pressure. Water (100 mL) was added and the reaction mixture was concentrated under reduced pressure, cooled and acidified with concentrated hydrochloric acid. The mixture was extracted with ether (2×100 mL) and the combined ether extracts were washed with brine (100 mL). The ether was filtered and distilled at atmospheric pressure. The residue was distilled through a short path still at 12 mm. to give 2.9 g (38%) of p-toluenethiol which was 95% pure by glpc.

EXAMPLE 18

Cleavage of 1-adamantanamine p-toluenesulfonamide. 1-Adamantanamine p-toluenesulfonamide (4 g, 0.13 mmol), n-propylamine (50 mL), and ethylenediamine (6.3 g, 0.11 mol) were placed in a 3 neck round bottomed flask equipped with a mechanical stirrer, condenser and thermometer. Lithium wire (0.64 g, 0.091 gram-atom) was added in two portions. Addition of one half of the lithium gave a dark color and the temperature rose to 42°. After an hour the temperature began to fall and the remainder of the lithium was added. The blue color dissipated over 45 min and the reaction mixture was poured onto ice and the resulting mixture was exacted with ether (3×50 mL). The ether was washed with brine and distilled at atmospheric pressure. The residue was sublimed at 90° (12 mm) to give 1.79 (91%) of 1-adamantanamine.

EXAMPLE 19

Reduction of 1-adamantanemethyl p-toluenesulfonate. Lithium (0.61 g, 0.087 gram-atom) was added to 1-adamantanemethyl p-toluenesulfonate (4.0 g, 0.012 mol) in n-propylamine (50 mL) and ethylenediamine (6 g, 0.10 mol) in a three neck flask equipped with a mechanical stirrer, condenser and a thermometer. Approximately half of the lithium was added at once. The remainder of the lithium was added after most of the first portion had dissolved. After 2 hr, the lithium had all reacted and the reaction mixture was poured onto ice and extracted with ether (2×50 mL). The ether was evaporated to give 1.9 g of crude 1-adamantanemethanol which was sublimed under vacuum to give 15 g (75%) of slightly yellow 1-adamantanemethanol. This sample showed the same nmr spectrum as authentic material.

EXAMPLE 20

Reduction of 1-adamantanemethyl methanesulfonate. Reduction of a sample of 1-adamantanemethyl methanesulfonate by the procedure described above gave a 70% yield of 1-adamantanemethanol. The invention has been described by reference to certain preferred embodiments and to examples; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing disclosure.

Having now described the invention, what is claimed is:

1. In a process of reducing an organic compound susceptible to dissolving metal reduction which comprises exposing the organic compound to a solution of lithium in a lower alkyl amine the improvement which comprises providing in such solution a polyamine, including at least two amino groups and selected from the group consisting of primary and secondary amino groups and mixtures thereof, wherein said polyamine comprises from 2 to 4 nitrogen atoms and from 2 to about 30 carbon atoms and R—$NH_2$, wherein R is chosen from the group consisting of lower alkyl radicals, having from 2 to 6 carbon atoms, including all straight and branched chain isomers thereof, optionally containing a lower alkyl alcohol, for a time sufficient to effect reduction.

2. The process of claim 1 wherein said polyamine is selected from the group consisting of ethylene diamine, N,N'-dimethylethylene-diamine, piperazine, diaminopropane, diaminobutane, dimethyl-diaminobutane and tris-(aminoethyl) amine.

3. The process of claim 1 wherein said polyamine is ethylenediamine.

4. The process of claim 1 wherein said polyamine is N,N'-dimethylethylenediamine.

5. The process of claim 1 wherein the reaction is conducted at ambient temperature and at ambient pressure.

6. The process of claim 5 wherein the temperature of the solution is maintained between 0° and 55° C. by heating or cooling as necessary.

7. The process of claim 1 wherein R—$NH_2$ is chosen from the group consisting of n-propylamine isopropylamine, n-butylamine and t-butylamine.

8. The process of claim 7 wherein R—$NH_2$ is n-propylamine.

9. The process of claim 3 wherein the reduction proceeds more rapidly than the same reaction mixture lacking any ethylenediamine.

10. The process of claim 1 wherein one or more double bonds of an aromatic hydrocarbon, which optionally has other substituents, is reduced.

11. The process of claim 1 wherein one or more functional groups chosen from the group consisting of a ketone and an oxime is reduced in the organic compound.

12. The process of claim 1 wherein an aryl sulfonamide is reduced to a corresponding thiophenol.

13. The process of claim 1 wherein naphthalene is reduced to isotetralin.

14. A process of reductively cleaving an organic compound susceptible to dissolving metal reduction comprising exposing the organic compound to a solution of lithium in a polyamine including at least two amino groups, selected from the group consisting of primary and secondary amino groups and mixtures thereof, wherein said polyamine comprises from 2 to 4 nitrogen atoms and from 2 to about 30 carbon atoms, and R—$NH_2$, wherein R is chosen from the group consisting of lower alkyl radicals, having from 2 to 6 carbon atoms including all straight and branched chain isomers thereof, optionally containing a lower alkyl alcohol, for a time sufficient to effect reductive cleavage.

15. The process of claim 1 wherein said polyamine is selected from the group consisting of ethylene diamine, N,N'-dimethylethylene diamine, piperazine, diaminopropane, diaminobutane, dimethyl diaminobutane and tris-(aminoethyl) amine.

16. The process of claim 1 wherein said polyamine is ethylenediamine.

17. The process of claim 1 wherein said polyamine is N,N'-dimethylethylenediamine.

18. The process of claim 14 wherein the reaction is conducted at ambient temperature and at ambient pressure.

19. The process of claim 18 wherein the temperature of the solution is maintained between 0° and 55° C. by heating or cooling as necessary.

20. The process of claim 16 wherein the cleavage proceeds more rapidly than in the same reaction mixture lacking any ethylenediamine.

21. The process of claim 14 wherein an aryl thioether is cleaved to provide an aryl thiol.

22. The process of claim 14 wherein an sulfonate ester is cleaved to provide an alcohol.

23. The process of claim 14 wherein a tertiary benzylamide is cleaved to provide a secondary amide.

24. The process of claim 23 wherein R—$NH_2$ is t-butylamine.

25. The process of claim 14 wherein a secondary or tertiary sulfonamide is cleaved to an amine.

26. The process of claim 14 wherein R—$NH_2$ is chosen from the group consisting of n-propylamine, isopropylamine, n-butylamine and t-butylamine.

27. The process of claim 26 wherein R—$NH_2$ is n-propylamine.

28. The process of claim 14 wherein said organic compound is N-benzylpilolactam, and the resulting product is trans-Pilolactam.

29. The process of claim 14 wherein said compound is N-benzyl, N-methyl decanoic acid amide, and the resulting product is N-methyl decanoic acid amide.

30. The process of claim 29 further comprising providing t-butanol in said solution and the resulting product is n-decanal.

31. The process of claim 10 wherein said aromatic hydrocarbon is selected from the group consisting of anisole, naphthalene and 3-methyl-2-cyclohexen-1-one and the resulting products are 1-methoxy-1, 3-cyclohexadiene, 1,4, 5,8-tetrahydronaphthalene and 3-methylcyclohexanone, respectively.

32. The process of claim 11 wherein said oxime is selected from the group consisting of 4-methylcyclohexanone oxime, and 4-methylcyclohexanone O-methyloxime and the resulting products are 4-methylcyclohexylamine.

33. The process of claim 11 wherein said oxime is selected from the group consisting of n-heptanal oxime and n-nonanal O-methyloxime and the resulting products are n-heptylamine and n-nonylamine, respectively.

34. The process of claim 12 wherein said aryl sulfonamide is morpholine p-toleunesulfonamide and the resulting product is p-toluenethiol.

35. The process of claim 21 wherein said arylthioether is thioanisole and the resulting product is thiophenol.

* * * * *

UNITED STATES PATENT AND TRADEMARK OFFICE
CERTIFICATE OF CORRECTION

PATENT NO. : 5,675,038
DATED : October 7, 1997
INVENTOR(S) : Dolby et al

It is certified that error appears in the above-indentified patent and that said Letters Patent is hereby corrected as shown below:

Column 3, line 20; delete "Solvent" and insert in place thereof --solvent--
Column 3, line 61; delete "We" and insert in place thereof --type--
Column 5, line 31; insert --in-- before "an"
Column 7, line 13; delete "(50%" and insert in place thereof --(50%)--
Column 9, line 50; delete "With" and insert in place thereof --with--
Column 10, line 61; delete "15" and insert in place thereof --1.5--

Signed and Sealed this

Thirty-first Day of March, 1998

Attest:

BRUCE LEHMAN

Attesting Officer     Commissioner of Patents and Trademarks